United States Patent [19]
Rowe et al.

[11] Patent Number: 5,842,567
[45] Date of Patent: Dec. 1, 1998

[54] QUICK RELEASE PACKAGE

[75] Inventors: T. Scott Rowe, Dana Point; Michael Meritt-Powell, Oceanside, both of Calif.

[73] Assignee: Alcon Laboratories, Inc., Fort Worth, Tex.

[21] Appl. No.: 969,092

[22] Filed: Nov. 12, 1997

[51] Int. Cl.$^6$ ............................................ B65D 81/113
[52] U.S. Cl. ........................ 206/364; 206/438; 206/464; 206/471; 220/263; 220/285
[58] Field of Search ................... 206/363–365, 206/368, 369, 63.5, 63.3, 438, 461, 464, 465, 470, 471; 220/4.21–4.23, 260, 262, 263, 264, 281, 284, 285; 53/492

[56] References Cited

U.S. PATENT DOCUMENTS

| | | | |
|---|---|---|---|
| 1,074,539 | 9/1913 | Baker | 220/285 |
| 4,799,503 | 1/1989 | Tahara | 220/260 |
| 4,809,868 | 3/1989 | Pomroy | 220/263 |
| 4,892,220 | 1/1990 | Foos | 220/284 |
| 4,899,877 | 2/1990 | Kiernan | 206/471 |
| 4,930,528 | 6/1990 | Hatakeyama | 206/263 |
| 5,050,623 | 9/1991 | Yuhara et al. | 220/263 |
| 5,176,272 | 1/1993 | Ryan . | |
| 5,474,179 | 12/1995 | Iosif et al. | 206/363 |
| 5,485,917 | 1/1996 | Early . | |
| 5,595,295 | 1/1997 | Lin | 206/470 |

*Primary Examiner*—Paul T. Sewell
*Assistant Examiner*—Luan K. Bui
*Attorney, Agent, or Firm*—Jeffrey S. Schira

[57] ABSTRACT

A package having two halves that are connected by a hinge. The hinge allows the halves to be folded against each other about a device and held in this position by snap/indentation pairs. A folded tab on one half rests against a detent on the other half. Pushing down on the folded tab causes the tab to straighten out and thereby push against the detent, eventually overcoming the frictional force of the snap/indentation pair closest to the tab and pushing the halves apart an amount sufficient to remove the device.

4 Claims, 6 Drawing Sheets

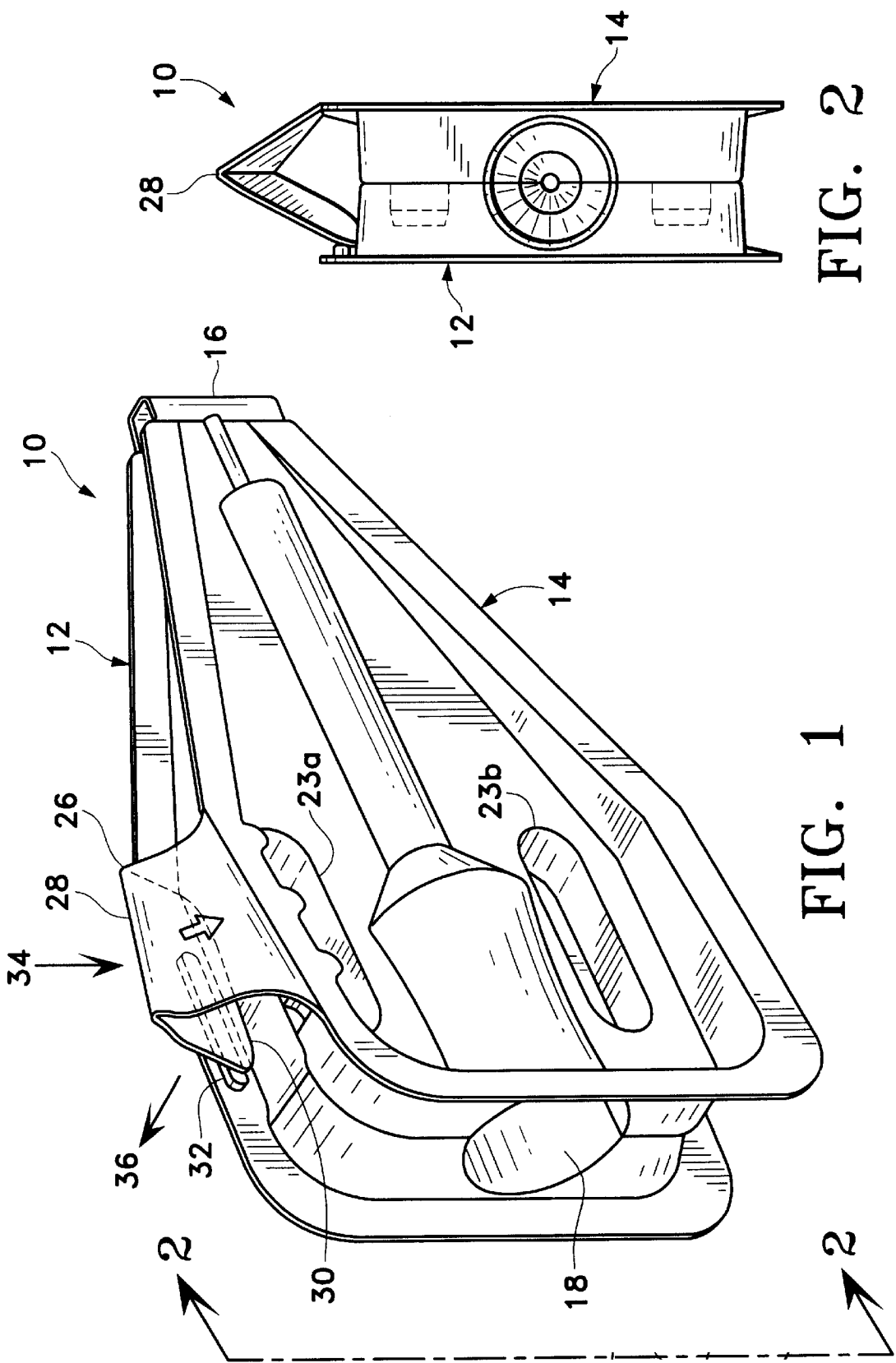

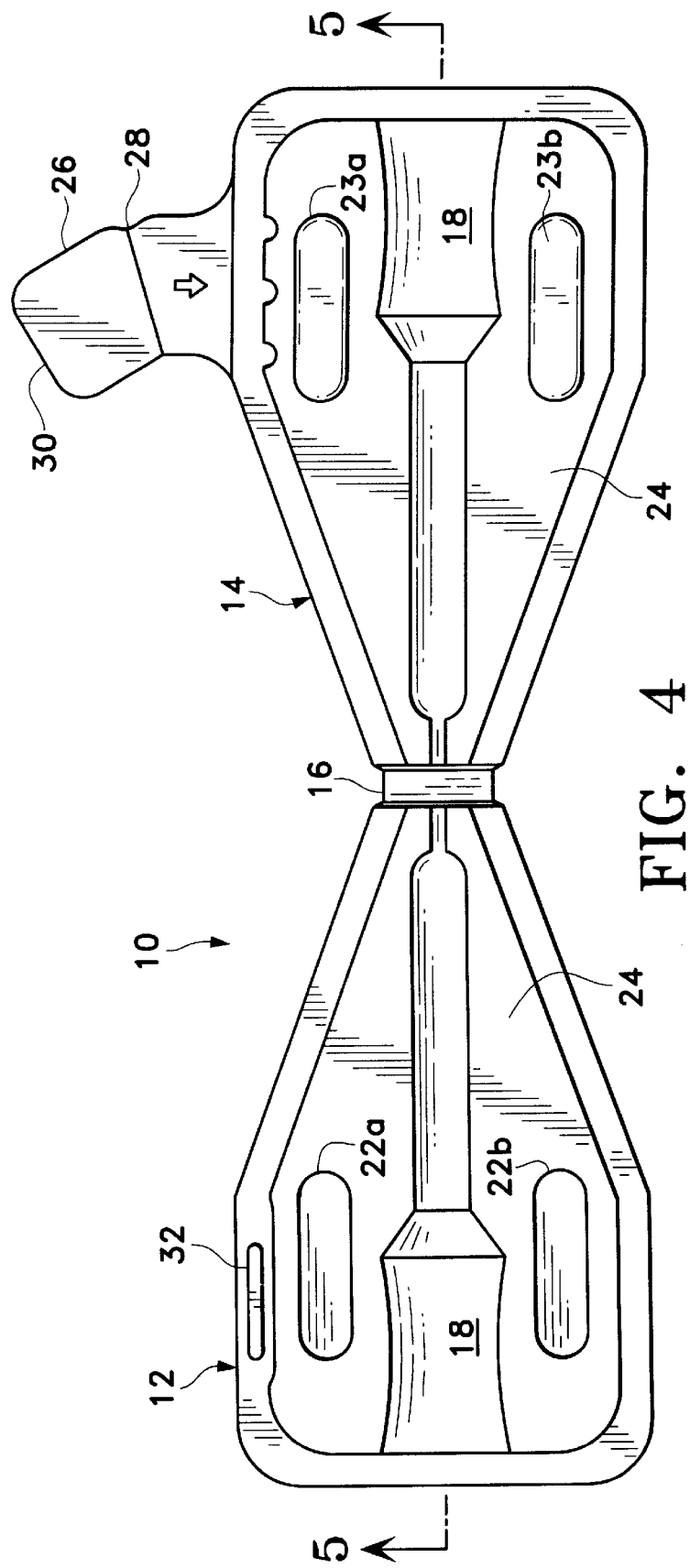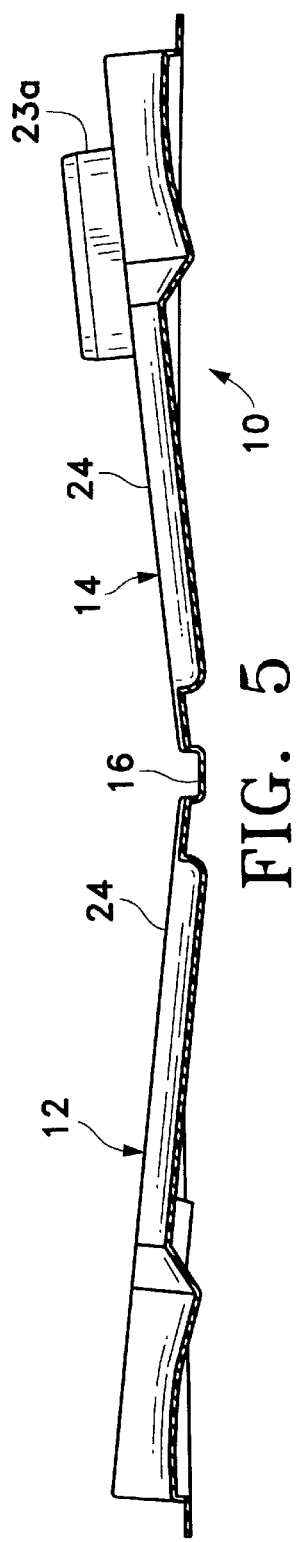

QUICK RELEASE PACKAGE

BACKGROUND OF THE INVENTION

This invention relates generally to the field of packaging and more particularly to sterilizable packaging used for medical devices.

Disposable medical devices such as probes, knives, scissors, cutters and catheters must be kept sterile and protected until opened. Generally speaking, these devices are sealed in a package and sterilized after sealing by gamma radiation or ethylene oxide gas. The typical package consists of a thermoformed plastic blister tray sealed air-tight by a spun polyester sheet (TYVEK®). Other packaging methods include two mating plastic trays that snap together with the device inside, the entire assembly then being sealed in an air-tight pouch.

While these prior art packaging method are effective in delivering a sterile device to the surgical field, opening these packages can sometimes be difficult, resulting in damage to or contamination of the device. Accordingly, a need continues for a sterilizable package for medical devices that protects the delicate product and is easy to open.

BRIEF SUMMARY OF THE INVENTION

The present invention improves upon the prior art by providing a package having two halves that are connected by a hinge. The hinge allows the halves to be folded against each other about a device and held in this position by snap indentation pairs ("snaps"). A folded tab on one half rests against a detent on the other half. Pushing down on the folded tab causes the tab to straighten out and thereby push against the detent, eventually overcoming the frictional force of the snap closest to the tab and pushing the halves apart an amount sufficient to remove the device.

Accordingly, one objective of the present invention is to provide a sterilizable package for medical devices.

Another objective of the present invention is to provide a sterilizable package for medical devices that protects the delicate product and is easy to open.

These and other advantages and objectives of the present invention will become apparent from the detailed description and claims that follow.

BRIEF DESCRIPTION OF THE DRAWING

FIG. 1 is a perspective view of the package of the present invention shown in the closed position.

FIG. 2 is a rear elevational view of the package of the present invention shown in the closed position.

FIG. 4 is a top plan view of the package of the present invention shown in the open position.

FIG. 5 is a cross-sectional view of the package of the present invention taken along line 5—5 of FIG. 4.

DETAILED DESCRIPTION OF THE INVENTION

Figure 3:
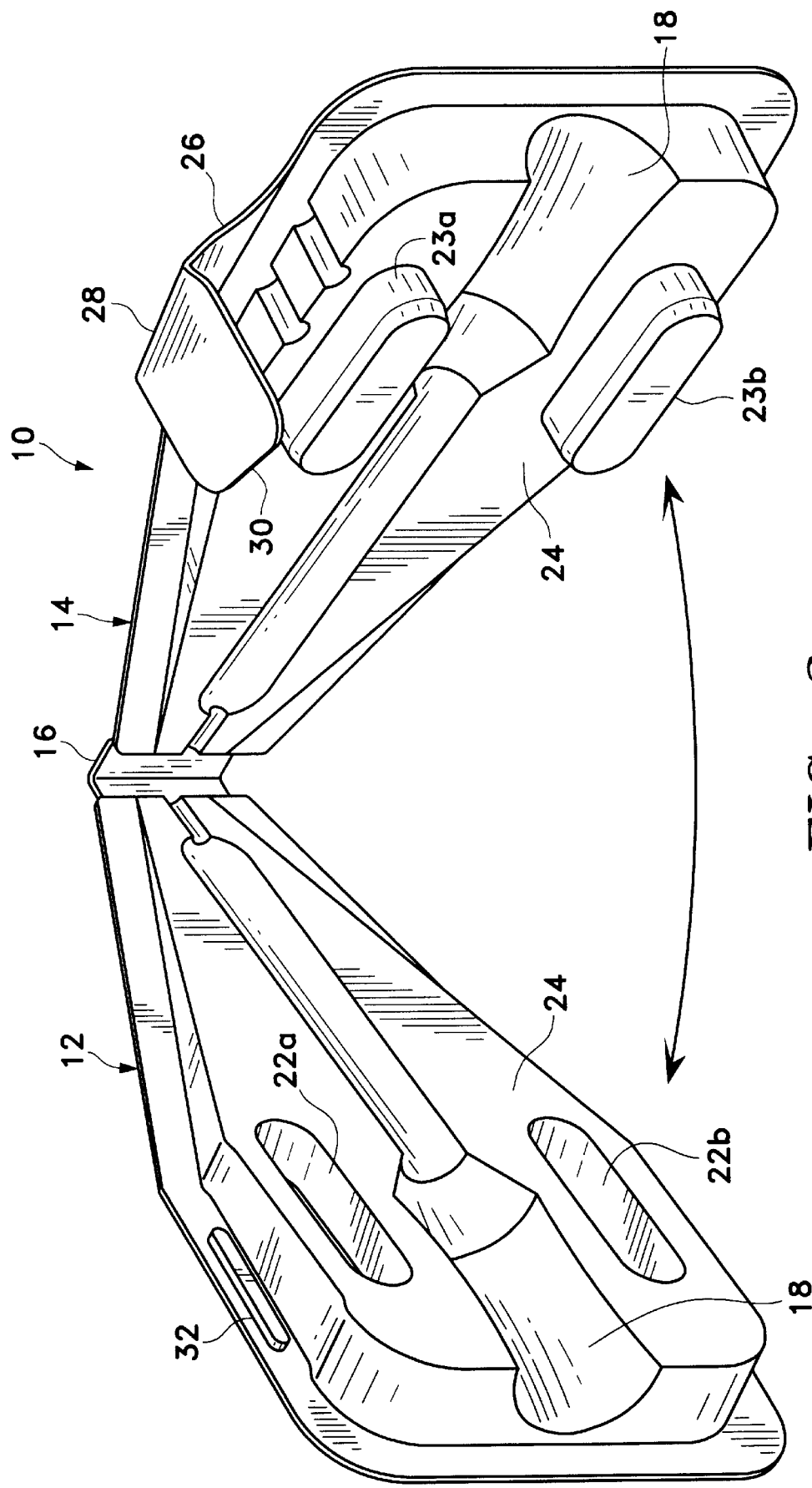
FIG. 3 is a perspective view of the package of the present invention shown in the open position.

As best seen in FIG. 3, package 10 of the present invention generally consists of a first half 12 and a second half 14 held together by hinge 16. First half 12, second half 14 and hinge 16 preferably are formed as a single piece from a suitable plastic, such as PETG (polyethylene terephathlate—ethylene glycol modified), polyvinyl chloride, polypropylene or polystyrene in a manner well-known in the art. Halves 12 and 14 may contain cavities 18 sized and shaped to hold a medical device, such as probe 20, securely when halves 12 and 14 are held together as described more fully below. Halves 12 and 14 are also formed with interlocking snap/indentation pairs 23a and 23b and 22a and 22b, respectively.

Figure 6:
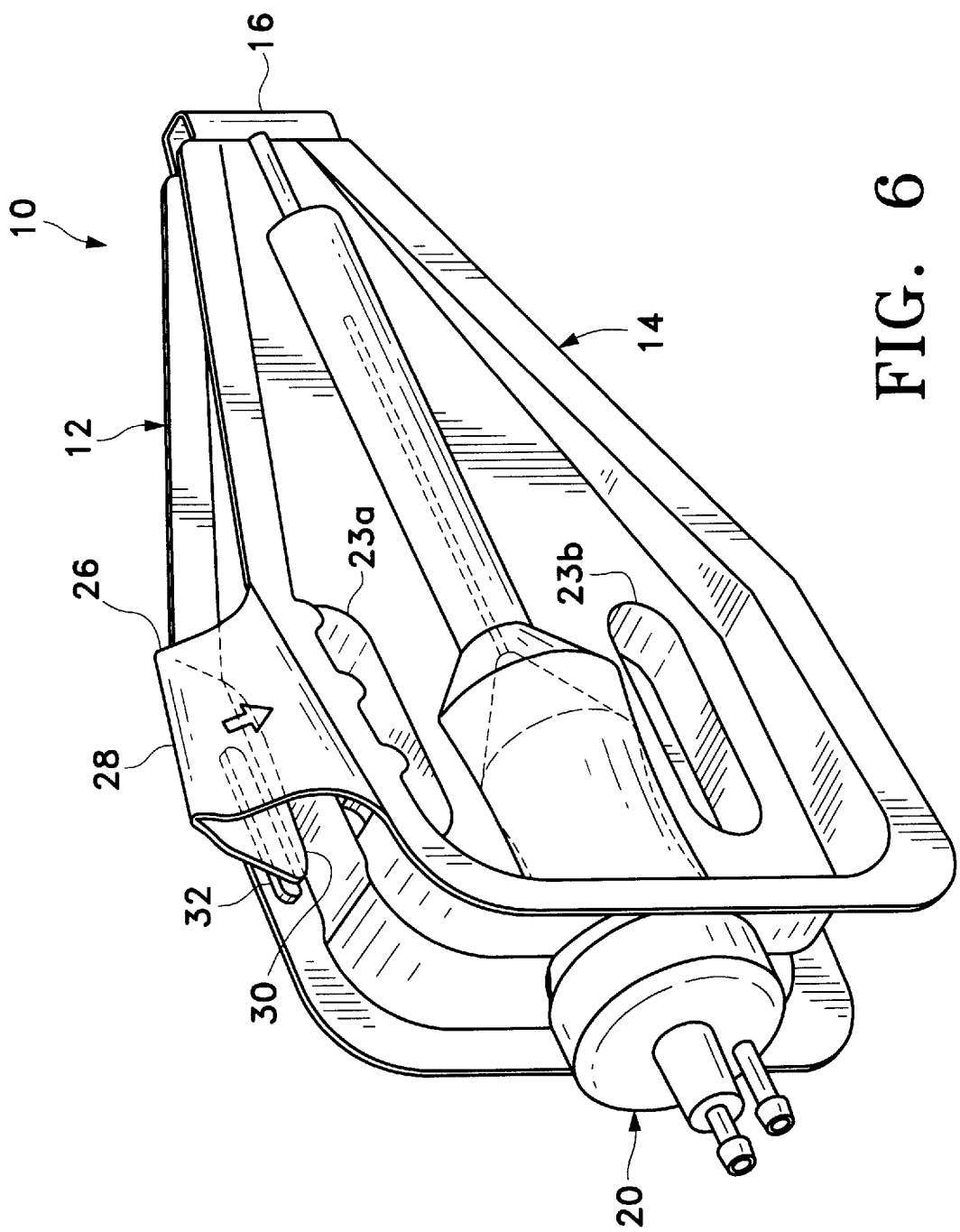
FIG. 6 is a perspective view of the package of the present invention shown in the closed position and containing a medical probe.
Figure 7:
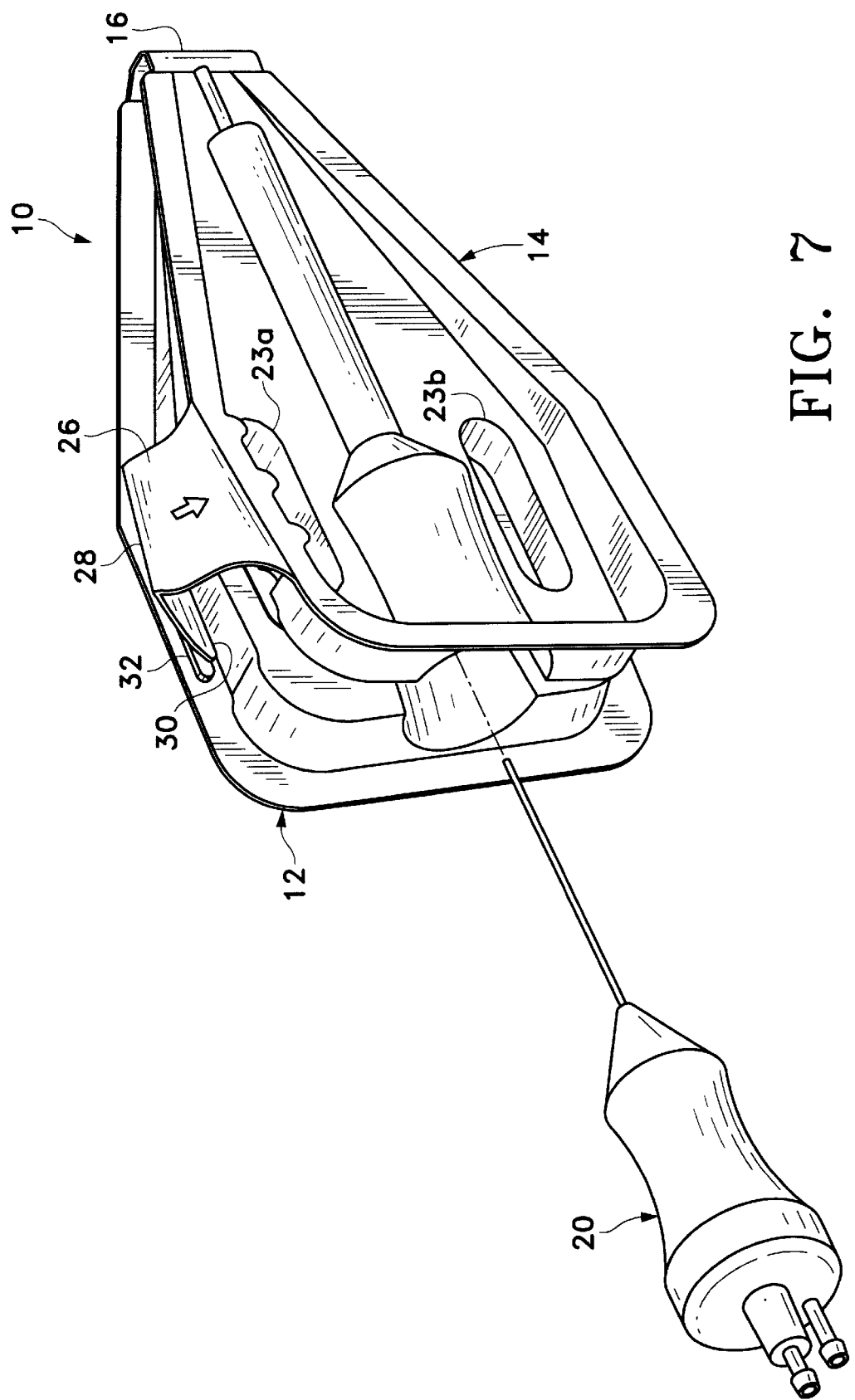
FIG. 7 is a perspective view of the package of the present invention shown in the open position and a medical probe being withdrawn from the package.
Figure 8:
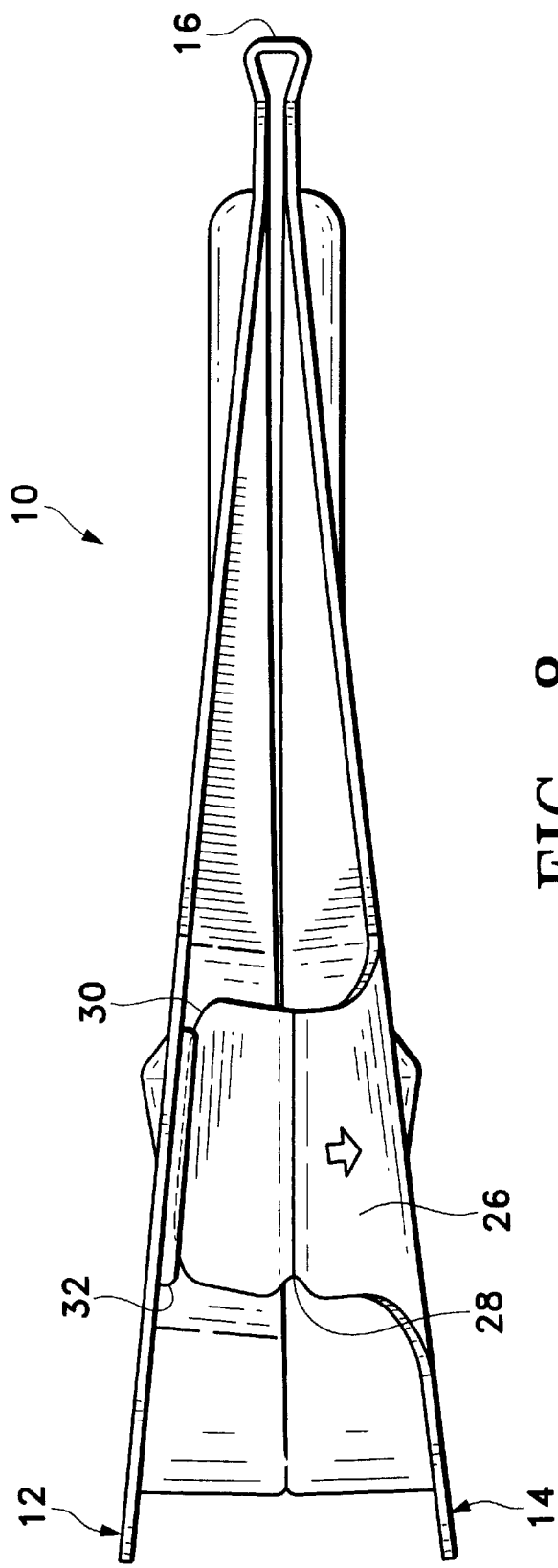
FIG. 8 is a top plan view of the package of the present invention shown in the closed position.

As shown in FIGS. 1, 2, and 6, in use, halves 12 and 14 are pivoted about hinge 16 until faces 24 touch each other and snaps 23a and 23b nest within indentations 22a and 22b, thereby locking halves 12 and 14 together with probe 20 held within cavities 18. Tab 26, which is integrally molded with and projects from second half 14 is folded along edge 28 so that free end 30 of tab 26 rests underneath detent 32 formed in first half 12. As shown by arrows 34 and 36 in FIG. 1, pushing down on edge 28 of tab 26 causes free end 30 of tab 26 to push outward against detent 32. When sufficient downward pressure is applied to edge 28, the outward force of free end 30 against detent 32 overcomes the frictional force holding snap 23a within indentation 22a so that halves 12 and 14 pivot about hinge 16 and snap/indentation pair 22b and 23b away from each other, as shown in FIG. 7, thereby allowing probe 20 to be withdrawn from cavities 18. Preferably, the release force necessary to overcome the frictional force of snap 23a within indentation 22a is less than the release force necessary to overcome the frictional force of snap 23b within indentation 22b.

This description is given for purposes of illustration and explanation. It will be apparent to those skilled in the relevant art that changes and modifications may be made to the invention described above without departing from its scope or spirit.

We claim:

1. A package, comprising:

a) a first half having a detent;

b) a second half having a foldable tab;

(c) the first and second halves having a first snap/indentation pair and a second snap/indentation pair, the first snap/indentation pair having a release force less than the second snap/indentation pair; and (d) a hinge pivotally connecting the first half and the second half so that when the tab is folded, a free end of the tab rests against the detent.

2. The package of claim 1 wherein the first half, the second half, the tab and the hinge are integrally molded from a thermoformed plastic.

3. The package of claim 1 further comprising a plurality of cavities formed in the first half and the second half.

4. A method of opening a package, the package having a first half with a detent, a second half with a foldable tab, a first snap/indentation pair, a second snap/indentation pair and a hinge pivotally connecting the first half and the second half so that when the tab is folded, a free end of the tab rests against the detent, the first snap is frictionally engaged in the first indentation and the second snap is frictionally engaged in the second indentation, the method comprising: depressing the folded tab with sufficient force so as to overcome the friction force holding the first snap/indentation pair together without overcoming the frictional force holding the second snap/indentation pair together, thereby pivoting the first half and the second half apart about the hinge an amount sufficient to allow removal of a device.

* * * * *